(12) United States Patent
Henry et al.

(10) Patent No.: US 9,528,139 B2
(45) Date of Patent: Dec. 27, 2016

(54) BIOCOMPATIBLE METHOD OF FUNCTIONALIZING SUBSTRATES WITH INERT SURFACES

(71) Applicants: Stephen Micheal Henry, Auckland (NZ); Stephen Robert Parker, Auckland (NZ)

(72) Inventors: Stephen Micheal Henry, Auckland (NZ); Stephen Robert Parker, Auckland (NZ)

(*) Notice: Subject to any disclaimer, the term of this patent is extended or adjusted under 35 U.S.C. 154(b) by 0 days.

(21) Appl. No.: 14/366,889

(22) PCT Filed: Dec. 19, 2012

(86) PCT No.: PCT/NZ2012/000242
§ 371 (c)(1),
(2) Date: Jun. 19, 2014

(87) PCT Pub. No.: WO2014/007649
PCT Pub. Date: Jan. 9, 2014

(65) Prior Publication Data
US 2014/0370538 A1 Dec. 18, 2014

(30) Foreign Application Priority Data

Dec. 19, 2011 (NZ) .................. 597207
Aug. 9, 2012 (NZ) .................. 601745

(51) Int. Cl.
*C12Q 1/02* (2006.01)
*C08G 64/42* (2006.01)
*G01N 33/543* (2006.01)

(52) U.S. Cl.
CPC .......... *C12Q 1/02* (2013.01); *C08G 64/42* (2013.01); *G01N 33/54353* (2013.01); *G01N 33/54393* (2013.01)

(58) Field of Classification Search
CPC .............................. G01N 33/54393
See application file for complete search history.

(56) References Cited

U.S. PATENT DOCUMENTS

2011/0042299 A1   2/2011  Zhang et al.

FOREIGN PATENT DOCUMENTS

| WO | WO 2009/087373 A1 | 7/2009 |
| WO | WO 2011/002310 A1 | 1/2011 |
| WO | WO 2012/099477 A1 | 7/2012 |

OTHER PUBLICATIONS

Dekkers et al. 1985, J of Applied Polymer Science, 30:2389-2400.*
Carmona-Ríbeiro, A.M.; "Interactions between Cationic Liposomes and Drugs or Biomolecules"; *An Acad. Bras. Ci.*, vol. 72 (1), pp. 39-43 (2000).
Cheng, C.J., et al; "Enhanced siRNA delivery into cells by exploiting the synergy between targeting ligands and cell-penetrating peptides"; *Biomaterials*; vol. 32, pp. 6194-6203 (2011).
Goodwin, A.P., et al; "Phospholipid-Dextran with a Single Coupling Point: A Useful Amphiphile for Functionalization of Nanomaterials"; *JACS Articles*; Published on Web Dec. 5, 2008, vol. 131, pp. 289-296 (2009), (XP007915884).
Munro, J.C., et al; "Adsorption of Lipid-Functionalized Poly(ethylene glycol) to Gold Surfaces as a Cushion for Polymer-Supported Lipid Bilayers"; *Langmuir*, vol. 20, pp. 3339-3349 (2004).
Xie, M., et al; "PEG-interspersed nitrilotriacetic acid-functionalized quantum dots for site-specific labeling of prion proteins expressed on cell surfaces"; *Biomaterials*; vol. 31, pp. 8362-8370 (2010).
Chemburu, S., et al; "Conjugated Polyelectrolyte Supported Bead Based Assays for Phospholipase $A_2$ Activity"; *J. Phys. Chem. B*; vol. 112, pp. 14492-14499 (2008).

* cited by examiner

*Primary Examiner* — Bin Shen
(74) *Attorney, Agent, or Firm* — Nixon & Vanderhye P.C.

(57) ABSTRACT

Method of functionalizing microspheres comprising immersing the microspheres in an aqueous dispersion of a construct of the structure F-S-L; and then washing the microspheres with an aqueous vehicle to provide the functionalized microspheres. The construct is of the structure:

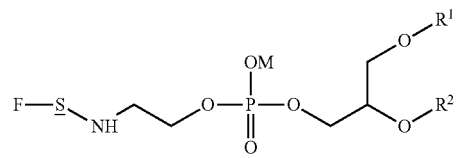

where F is a functional moiety, M is a monovalent cation, $R^1$ and $R^2$ are independently a $C_{14\text{-}20}$ acyl, alkyl or alkenyl group, and S is a spacer selected to provide a construct that is dispersible in water.

4 Claims, 16 Drawing Sheets

A

B

A

B

BIOCOMPATIBLE METHOD OF FUNCTIONALIZING SUBSTRATES WITH INERT SURFACES

This application is the U.S. national phase of International Application No. PCT/NZ2012/000242 filed 19 Dec. 2012 which designated the U.S. and claims priority to New Zealand Patent Application Nos. 597207, filed 19 Dec. 2011, and 601745, filed 9 Aug. 2011, the entire contents of each of which are hereby incorporated by reference.

FIELD OF INVENTION

The invention relates to a biocompatible method of functionalising inert surfaces for use in biological applications. In particular, the invention relates to a biocompatible method of functionalising the inert surface of porous membranes and microspheres or nanospheres.

BACKGROUND ART

Filter membranes are routinely used in the analysis and preparation of biological samples. The surface of the substrate used in the manufacture of such membranes is purposefully selected to be antifouling, i.e. resistant to non-specific binding of components of the biological sample, and chemically inert. Microbeads and microspheres are used for the isolation and separation of biomolecules from complex mixtures. Reactive molecules are adsorbed or coupled to the surface of the beads or spheres. When the beads or spheres are superparamagnetic biomagnetic separation techniques may be employed. Membranes and microbeads or microspheres can be manufactured from various natural and synthetic materials including glass, metal, e.g. gold, and polymers, e.g. polycarbonate, polyethylene and polystyrene. Polystyrene is commonly used in biological applications as proteins readily adsorb onto its surface. Glass has limited use because of the limited ability to functionalise its surface. It is an object of the present invention to provide a biocompatible method of localising functional moieties to the inert surface of a substrate or at least to provide the public with a useful choice.

STATEMENT OF INVENTION

In a first aspect the invention provides a method of functionalising an inert surface of a substrate comprising the step of contacting the surface of the substrate with an aqueous dispersion of a construct of the structure F-S-L, where F is a functional moiety, S is a spacer selected to provide a construct that is dispersible in water, and L is a diacyl- or dialkyl-glycerophospholipid.

Preferably, the method comprises the steps of:
1. contacting the surface of the substrate with an aqueous dispersion of a construct of the structure F-S-L; and then
2. washing the surface of the substrate with an aqueous vehicle to provide the functionalised surface.

Preferably, the inert surface consists of a substance selected from the group consisting of: glass, silver, polyamide, polycarbonate, polypropylene, polyethersulfone, polytetrafluoroethylene and polyvinylidene fluoride. More preferably, the inert surface is other than polystyrene. Preferably, the substrate is a fibre, membrane or microsphere.

Preferably, the contacting the surface of the substrate is by immersing the substrate in the aqueous dispersion of the construct. Most preferably, the contacting the surface of the substrate by immersing the substrate in the aqueous dispersion of the construct is when the substrate is a fibre or microsphere.

Preferably, the contacting the surface of the substrate is by flooding the surface of the substrate with the aqueous dispersion of the construct. Most preferably, the contacting the surface of the substrate is by flooding the surface of the substrate with the aqueous dispersion of the construct when the substrate is a membrane.

In a first embodiment of the first aspect of the invention the substrate is a membrane comprised of cross-linked, fused or woven fibres. More preferably, the membrane is a filtration membrane. In a second embodiment of the first aspect of the invention the substrate is a microsphere. More preferably, the microsphere is a polycarbonate microsphere.

Preferably, the construct is a water dispersible construct of the structure:

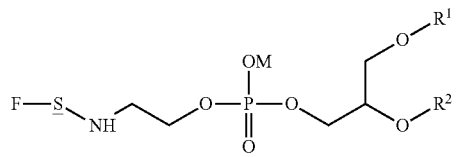

where F is a functional moiety, M is a monovalent cation, $R^1$ and $R^2$ are independently a $C_{14-20}$ acyl, alkyl or alkenyl group, preferably a $C_{16-18}$ acyl, alkyl or alkenyl group, and S is a spacer selected to provide a construct that is dispersible in water. More preferably, the construct is a water dispersible construct of the structure:

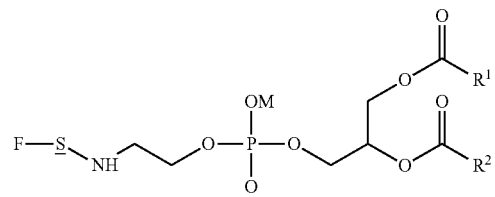

where $R^1$ and $R^2$ are independently a $C_{13-19}$ alkyl or alkenyl group, preferably a $C_{15-17}$ alkyl or alkenyl group. Yet more preferably, F-S- is of the structure F-$S_1$-$S_2$-$S_3$- where:

$S_1$ is 2-aminoethyl, 3-aminopropyl, 4-aminobutyl, or aminopentyl, $S_2$ is absent or

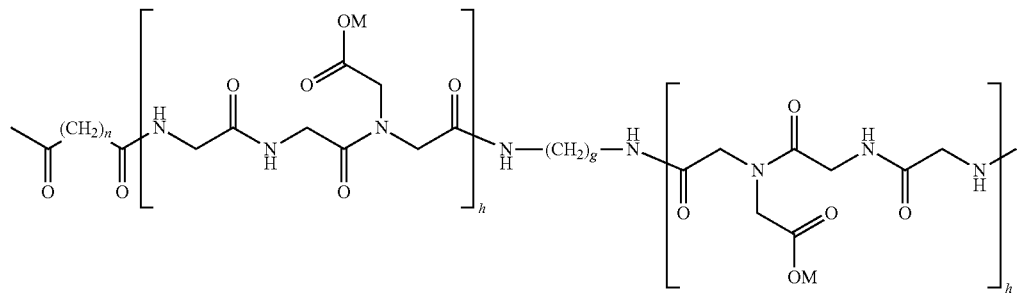

where g is the integer 1, 2 or 3, h is the integer 1, 2, 3 or 4, n is the integer 2, 3, 4 or 5, and $S_3$ is —$CO(CH_2)_2CO$—, —$CO(CH_2)_3CO$—, —$CO(CH_2)_4CO$— or —$CO(CH_2)_5CO$— when F is a mono-, di-, tri- or oligosaccharide;

$S_1$ is

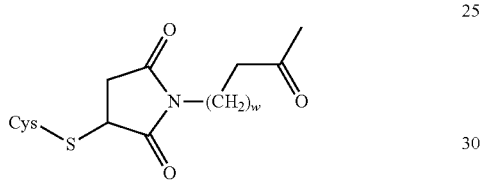

where w is the integer 1 or 2, $S_2$ is

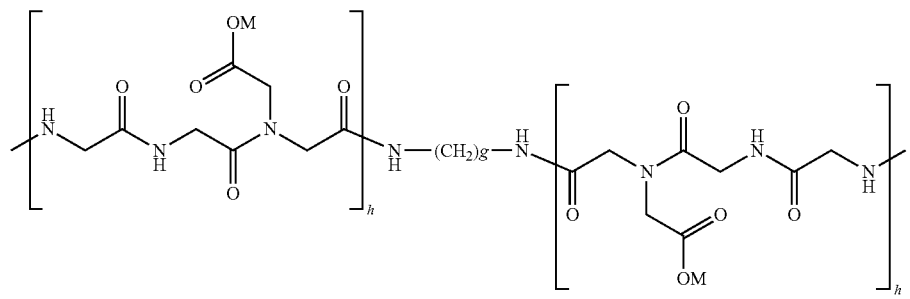

where g is the integer 1, 2 or 3 and h is the integer 1, 2, 3 or 4, and $S_3$ is —$CO(CH_2)_2CO$—, —$CO(CH_2)_3CO$—, —$CO(CH_2)_4CO$— or —$CO(CH_2)_5CO$— when F is an oligopeptide;

$S_1$ is

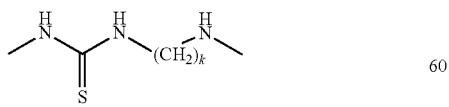

where k is the integer 4, 5 or 6, $S_2$ is absent and $S_3$ is $CO(CH_2)_2CO$—, —$CO(CH_2)_3CO$—, —$CO(CH_2)_4CO$— or —$CO(CH_2)_5CO$— when F is a fluorophore of fluorescein or a derivative thereof; or $S_1$ is

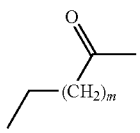

where m is the integer 1 or 2, $S_2$ is

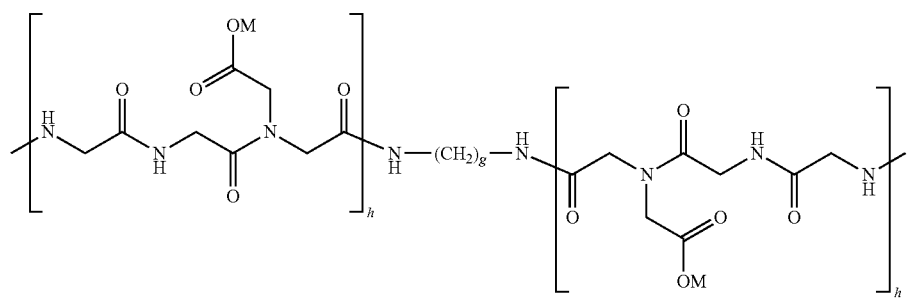

where g is the integer 1, 2 or 3 and h is the integer 1, 2, 3 or 4, and $S_3$ is —CO(CH$_2$)$_2$CO—, —CO(CH$_2$)$_3$CO—, —CO(CH$_2$)$_4$CO— or —CO(CH$_2$)$_5$CO— when F is biotin.

Most preferably, the construct is a water dispersible construct of the structure F-S-L as described in one or more of the specifications accompanying international application nos. PCT/NZ2005/000052 (publ. no. WO 2005/090368), PCT/NZ2006/000245 (publ. no. WO 2007/035116), PCT/NZ2008/000239 (publ. no. WO 2009/035347), PCT/NZ2008/000266 (publ. no. WO 2009/048343), PCT/NZ2010/000111 (publ. no. WO 2010/143983), PCT/NZ2012/000012 (publ. no. WO 2012/121610), PCT/NZ2012/000029 (publ. no. WO 2012/118388) and PCT/NZ2012/000156 (unpublished).

Typically, L is 1,2-O-dioleoyl-sn-glycero-3-phosphatidylethanolamine (DOPE) and 1,2-O-distearyl-sn-glycero-3-phosphatidylethanolamine (DSPE), most often 1,2-O-dioleoyl-sn-glycero-3-phosphatidylethanolamine (DOPE).

In a second aspect the invention provides a substrate comprising a construct of the structure F-S-L localised to its surface where the surface is inert, F is a functional moiety, S is a spacer selected to provide a construct that is dispersible in water, and L is a diacyl- or dialkyl-glycerophospholipid. Preferably, the inert surface is polycarbonate.

In a first embodiment of the second aspect the substrate is fibre. In a second embodiment of the second aspect the substrate is membrane. In a third embodiment of the second aspect the substrate is a microsphere.

In a third aspect the invention provides a filter assembly comprising a membrane functionalised according to the method of the first aspect of the invention. Preferably, the filter assembly comprises a membrane functionalised according to the method of the first aspect of the invention and sealed between an inlet housing and an outlet housing.

In the description and claims of this specification the following acronyms, terms and phrases have the meaning provided. "Biocompatible" means not harmful or toxic to living tissue. "Comprising" means "including", "containing" or "characterized by" and does not exclude any additional element, ingredient or step. "Consisting of" means excluding any element, ingredient or step not specified except for impurities and other incidentals. "FSL-Biotin" means the water soluble construct of the structure:

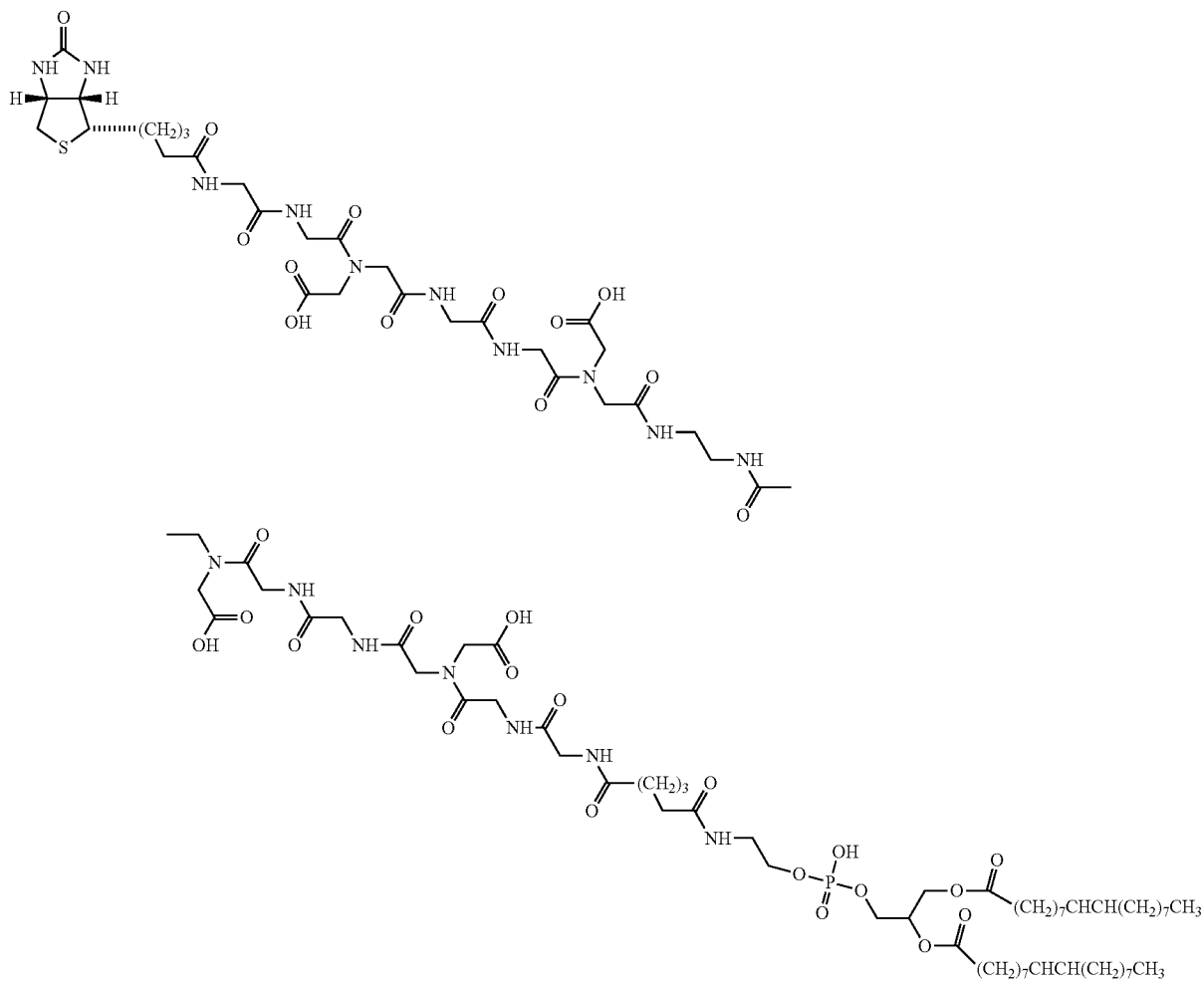

40 as described in the specification accompanying international application no. PCT/NZ2008/000266 (publ. no. WO 2009/048343). "FSL-A$_{tri}$" means the water soluble construct of the structure:

cyte" means a cell modified by incorporation into the cell membrane of a construct of the general structure F-S-L (where F is a functional moiety, S is a spacer selected to provide a water dispersible construct and L is a lipid).

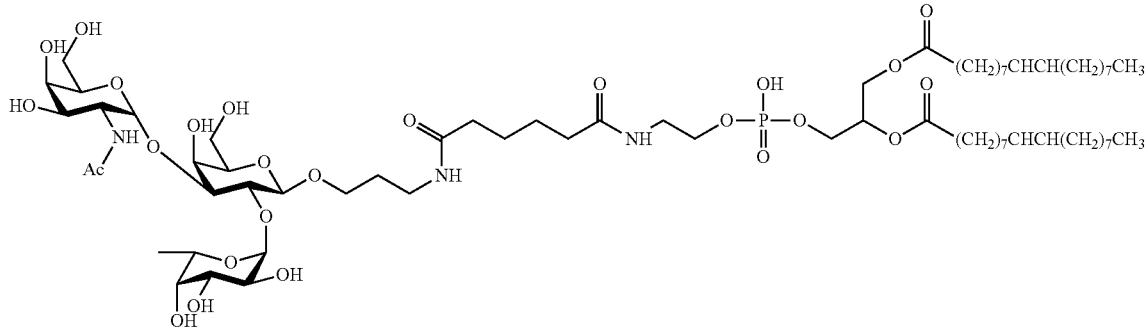

60 as described in the specification accompanying international application no. PCT/NZ2005/000052 (publ. no. WO 2005/090368). "Hydrophilic" means having a tendency to mix with, dissolve in, or be wetted by water; "hydrophobic" means tending to repel or fail to mix with water. "Inert" mean non-reactive under biocompatible conditions. "Kode- "Kodevirion" means an enveloped virus particle modified by incorporation into the enveloping membrane of a construct of the general structure F-S-L (where F is a functional moiety, S is a spacer selected to provide a water dispersible construct and L is a lipid). "Localised" means associated with a surface by non-covalent interactions and "localising"

and "localisation" have a corresponding meaning. "Non-polyhydric" means the material or molecule that is the substance contains substantially no hydroxyl groups and specifically excludes substances such as cellulose and silica gel. "Non-reactive" means covalent bonds are neither broken nor formed. "PBS" denotes phosphate buffered saline. "PCV" denotes packed cell volume. "Plasma" means the colourless fluid part of blood or lymph, in which corpuscles or fat globules are suspended. "Polyhydric" means the material or molecule that is the substance contains a plurality of free hydroxyl groups. "RBC" denotes red blood cell. "Saline" means a solution of one or more salts. "Serum" means the amber-coloured, protein-rich liquid which separates out when blood coagulates. "Synthetic" means prepared by chemical synthesis. "Water soluble" means, in the context of describing the properties of a construct, that a stable, single phase system is formed in the absence of organic solvents or detergents when an amount of the construct sufficient to provide a final concentration of at least 100 µg/mL is contacted with water at a temperature of 25° C. In this context the terms "dispersible" and "soluble" are used synonymously.

It is to be understood that use of the term "non-polyhydric" as a descriptor of a substance is not intended to exclude substances that are hydrophilic. A non-polyhydric substance may be either hydrophilic or hydrophobic according to its chemical composition. Accordingly, a non-polyhydric substance may be either wettable or water repellent according to its chemical composition, but a non-polyhydric polymer will generally be inert under biocompatible conditions.

The terms "first", "second", "third", etc. used with reference to elements, features or integers of the subject matter defined in the Statement of Invention and Claims, or when used with reference to alternative embodiments of the invention are not intended to imply an order of preference.

Where concentrations or ratios of reagents are specified the concentration or ratio specified is the initial concentration or ratio of the reagents. Where values are expressed to one or more decimal places standard rounding applies. For example, 1.7 encompasses the range 1.650 recurring to 7.499 recurring.

In the absence of further limitation the use of plain bonds in the representations of the structures of compounds encompasses the distereoisomers, enantiomers and mixtures thereof of the compounds, with the proviso that where the representation is of the structure of a compound or a portion of a structure of a compound of biological origin, the structure or portion of the structure represented is limited to structures or portions of structures that are functionally equivalent to the structure or portion of the structure of the compound of biological origin.

The invention will now be described with reference to embodiments or examples and the figures of the accompanying drawings pages.

BRIEF DESCRIPTION OF DRAWINGS

FIG. 7) following mixing with a solution of avidin conjugated AlexaFlour™ 488 and examined by light (A) and fluorescent (B) microscopy.

FIG. 7) following mixing with a solution of streptavidin then FSL-Biotin kodecytes (RBCS) [20× magnification (A), 100× magnification (B)].

DETAILED DESCRIPTION

Figure 1:
FIG. 1. Illustration of the hypothetical mechanism by which the water dispersible constructs are localised to the surface of a substrate as either a monolayer (A) or bilayer (B).
Figure 1:
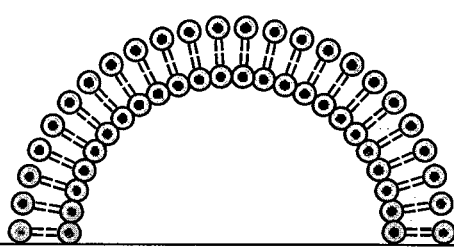
Figure 2:
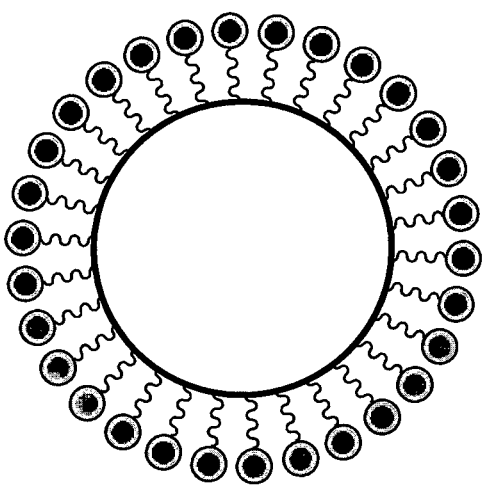
FIG. 2. Illustration of the hypothetical mechanism by which the water dispersible constructs are localised to the surface of a fibre or sphere as either a monolayer (A) or bilayer (B).
Figure 2:
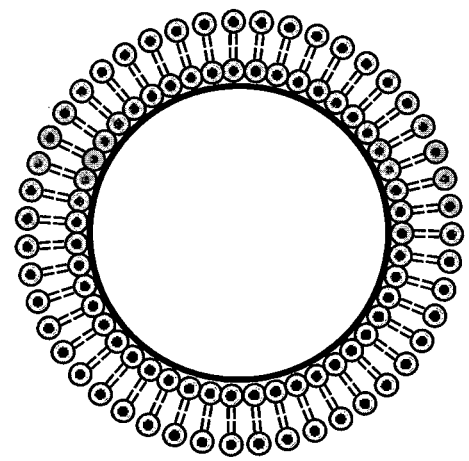

In the method of the invention a functionalising moiety is localised (as defined) to the surface of a substrate where the surface is inert (as defined). The association between the construct F-S-L comprising the functionalising moiety (F) is sufficiently strong under biocompatible (as defined) conditions to permit use in a variety of biological applications including sample analysis and preparation. These biological applications include blocking and washing steps using aqueous solutions that, save for the strength of the association between the construct and the surface of the substrate, would be expected to remove the functionalising moiety. Surprisingly it has been found that the association between the construct and the surface is strong enough to be maintained during repeated washing steps irrespective of the hydrophobicity or hydrophilicity of the surface of the substrate. Without wishing to be bound by theory it is believed the strength of the association between the construct and the surface of the substrate could be attributable to the construct spontaneously forming a layer enveloping the surface of the substrate. It is suggested that such envelopment is favoured by the substrate being in the form of a fibre or thread, but this suggestion does not exclude the possibility that envelopment occurs in discrete areas of the surface of the substrate, e.g. as a lining of the inner walls of the channels present in a porous substrate, such as a filter membrane. Without wishing to be bound by theory it is hypothesised that the formation of mono- or bilayers as illustrated schematically in FIGS. 1 and 2 is thermodynamically favoured, possibly contributed to by the entropic gain attributable to the exclusion of water from the surface, thereby explaining the broad range of inert surfaces to which the method of the invention may be applied.

Products supplied under the trade name PHENEX™ (Phenomenex) are examples of polyamide (NYLON™) filter membranes. Products supplied under the trade name GH POLYPRO™ (Gelman) and the trade name METRICEL™ (Pall Corporation) are examples of polypropylene filter membranes. Products supplied under the trade name GELMAN TF™ (Gelman) are examples of filter membranes with a polytetrafluoroethylene (TEFLON™) surface. Despite the surface of these substrates ranging from the hydrophobic to the hydrophilic, all have been shown to be substrates capable of being functionalised according to the method of the invention. Other substrates that may be functionalised according to the method of the invention include the products supplied under the trade name DURAPOR™ (Millipore) which are filter membranes with a polyvinylidene fluoride (KYNAR™, HYLAR™) surface.

The surface of the substrate constituting a filter membrane employed in the analysis and preparation of biological samples, such as plasma and serum, is purposefully selected to be antifouling. The antifouling properties prevent, or at least substantially mitigate, non-specific binding of components of the biological samples to the membrane. The avoidance of non-specific binding to the filter membrane is desirable to avoid clogging of the membrane and cross-contamination of biological samples with repeated use. The antifouling characteristic of the surface of the substrate constituting a filter membrane necessarily limits the ability to introduce functionalities that promote selective binding of minor components of the biological sample to the membrane and consequential concentration in situ or following elution.

The method of the invention permits the functionalization of a surface that has purposefully been selected to be antifouling. The functionalization is achieved by the localisation of the functionalising moiety to the surface under conditions that are biocompatible and do not affect the structural integrity of the substrate. Use of the method of the invention enables novel sample analysis and preparation procedures to be employed as illustrated with reference to the Figures of the accompanying drawings and the following examples.

EXAMPLE 1

Dispersions of the aminopropyl derivative of blood group A trisaccharide (A$_{tri}$-S$_1$) and the construct A$_{tri}$-sp-Ad-DOPE (FSL-A) were prepared at a concentration of 0.2 mM in PBS containing 0.01% polyoxyethylene (20) sorbitan monolaurate (TWEEN™ 20) and 1% inkjet ink (magenta).

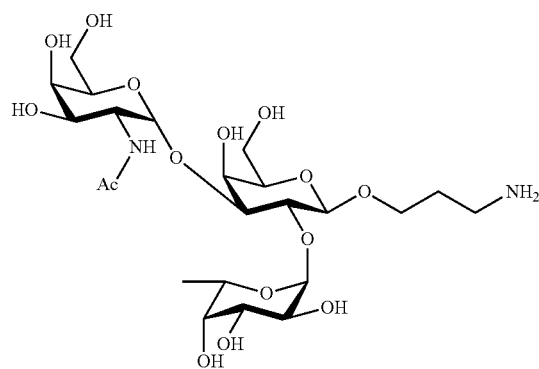

A$_{tri}$-S$_1$ (as described in the specification accompanying international application no. PCT/NZ2005/000052 (publ. no. WO 2005/090368))

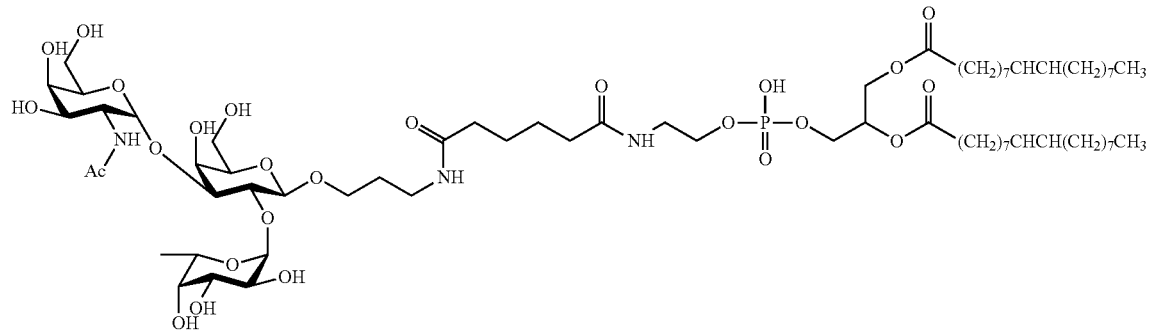

FSL-A (as described in the specification accompanying international application no. PCT/NZ2005/000052 (publ. no. WO 2005/090368))

Figure 3:
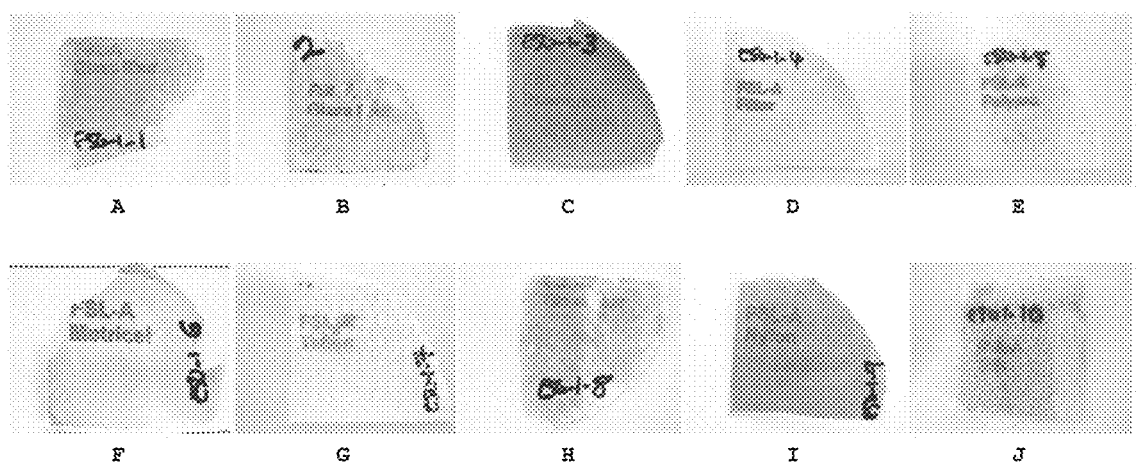
FIG. 3. Appearance of the surface of substrates following printing and immunostaining using a 1 in 5 dilution in BSA of anti-A immunoglobulin (EPICLONE™ monoclonal, CSL Limited) according to the method described in Example 1: A—glass fibre filter paper GC-50 (Advanetc); B—glass microfiber filter GF/B (Whatman); C—nylon membrane filter 0.2 µm (Phenomenex); D—filter paper 1 (Whatman); E—polypropylene filter membrane (Gelman Sciences); F—METRICEL™ filter membrane GA-3 1.2 µm (Gelman Sciences); G—TEFLON™ filter membrane TF-200 0.2 µm (Gelman Instrument Company); H—glass fibre filter A/E (Pall Life Sciences), I—nylon 66 filter membrane 0.45 µm (Schleicher & Schuell) and J—silk.
Figure 4:
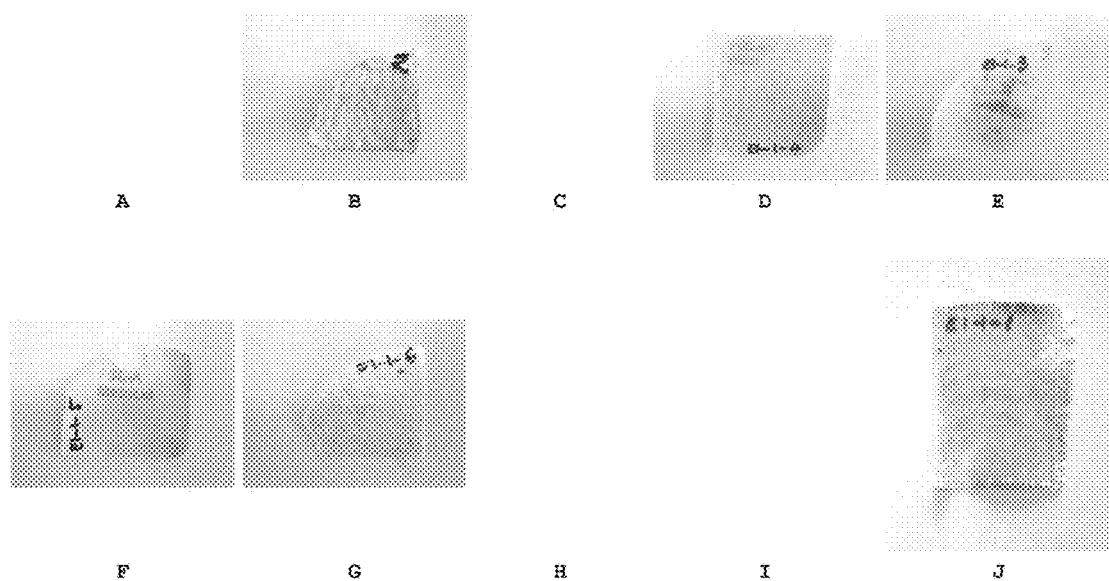
FIG. 4. Appearance of the surface of substrates following printing and immunostaining using a 1 in 2 dilution in BSA of O group serum according to the method described in Example 1: A—glass fibre filter paper GC-50 (Advanetc); B—glass microfiber filter GF/B (Whatman); C—nylon membrane filter 0.2 µm (Phenomenex); D—filter paper 1 (Whatman); E—polypropylene filter membrane (Gelman Sciences); F—METRICEL™ filter membrane GA-3 1.2 µm (Gelman Sciences); G—TEFLON™ filter membrane TF-200 0.2 µm (Gelman Instrument Company); H—glass fibre filter A/E (Pall Life Sciences), I—nylon 66 filter membrane 0.45 µm (Schleicher & Schuell) and J—silk.

The dispersions were loaded into separate ink cartridges of an EPSON STYLUS™ T21 piezoelectric inkjet printer. The identity of the dispersion and substrate were printed onto samples of the following substrates: glass fibre filter paper GC-50 (Advanetc); glass microfiber filter GF/B (Whatman); nylon membrane filter 0.2 µm (Phenomenex); filter paper 1 (Whatman); polypropylene filter membrane (Gelman Sciences); METRICEL™ filter membrane GA-3 1.2 µm (Gelman Sciences); TEFLON™ filter membrane TF-200 0.2 µm (Gelman Instrument Company); glass fibre filter A/E (Pall Life Sciences), nylon 66 filter membrane 0.45 µm (Schleicher & Schuell) and silk. The printed samples of substrate were then immersed in a solution of 2% (w/v) bovine serum albumin (BSA) in PBS for 1 hour prior to being rinsed and the surface of the substrate being flooded with a 1 in 5 dilution in BSA of anti-A immunoglobulin (EPICLONE™ monoclonal, CSL Limited) and incubated for 30 minutes, or flooded with a 1 in 2 dilution in BSA of O group serum and incubated for 1 hour. The surfaces of the substrates were then washed 6 times with PBS prior to being flooded with a 1:400 dilution of alkaline phosphatase conjugated sheep anti-mouse immunoglobulin (Chemicon) and incubated for 30 minutes. The surfaces of the substrates were then washed 6 times with PBS followed by a washing of substrate buffer (100 mM Tris, 100 mM NaCl, 50 mM MgCl$_2$, pH 9.5). The substrate buffer washed surfaces of the substrates were then flooded with a 1 in 50 dilution in substrate buffer of the chromogenic substrate (18.75 mg/mL nitro blue tetrazolium chloride and 9.4 mg/mL 5-bromo-4-chloro-3-indolyl phosphate, toluidine salt) (NBTC-BCIP) in 67% DMSO (Roche)) for about 10 minutes. The chromogenic reaction was stopped by rinsing the surface of each substrate with deionised water. The appearance of the surface of each substrate following incubation with the chromogenic substrate is provided in FIG. 3 and FIG. 4. It will be observed that there was no immunostaining of the surface of the substrate in the region where the aminopropyl derivative of the A trisaccharide (A$_{tri}$-sp-NH$_2$) was printed. It is assumed that the aminopropyl derivative of the A trisaccharide (A$_{tri}$-sp-NH$_2$) was washed away during the immunostaining procedure.

EXAMPLE 2

Dispersions of the construct B$_{tri}$-sp-Ad-DOPE (FSL-B) and its monoacyl counterpart (monoacyl-B) were prepared at a concentration of 0.4 mM in PBS containing 0.01% polyoxyethylene (20) sorbitan monolaureate (TWEEN™ 20) and 1% inkjet ink (magenta).

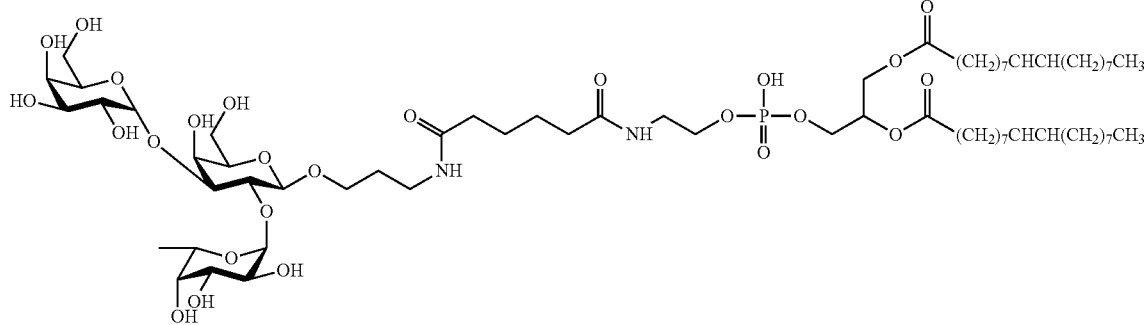

FSL-B (as described in the specification accompanying international application no. PCT/NZ2005/000052 (publ. no. WO 2005/090368))

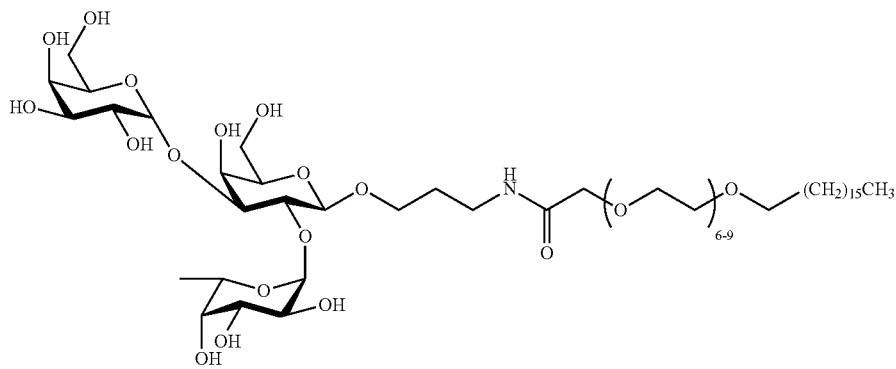

Monoacyl-B (as described in the specification accompanying international application no. PCT/NZ2005/000052 (publ. no. WO 2005/090368))

Figure 5:
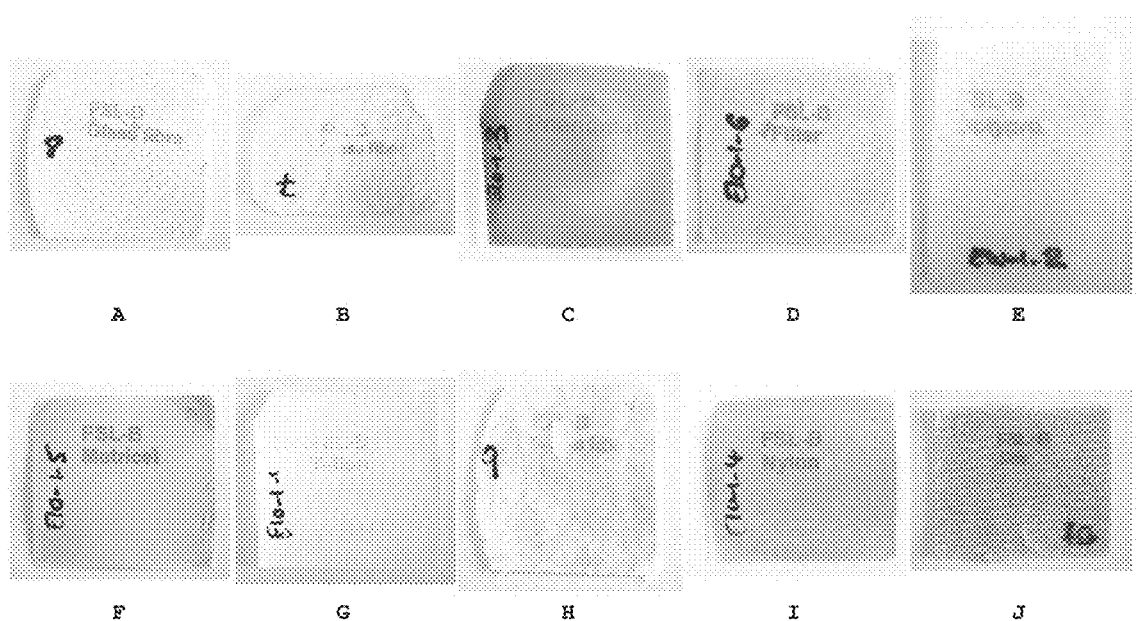
FIG. 5. Appearance of the surface of substrates following printing and immunostaining using a 1 in 5 dilution in BSA of anti-B immunoglobulin (EPICLONE™ monoclonal, CSL Limited) according to the method described in Example 2: A—glass fibre filter paper GC-50 (Advanetc); B—glass microfiber filter GF/B (Whatman); C—nylon membrane filter 0.2 µm (Phenomenex); D—filter paper 1 (Whatman); E—polypropylene filter membrane (Gelman Sciences); F—METRICEL™ filter membrane GA-3 1.2 µm (Gelman Sciences); G—TEFLON™ filter membrane TF-200 0.2 µm (Gelman Instrument Company); H—glass fibre filter A/E (Pall Life Sciences), I—nylon 66 filter membrane 0.45 µm (Schleicher & Schuell) and J—silk.

The dispersions were loaded into separate ink cartridges of an EPSON STYLUS™ T21 piezoelectric inkjet printer. The identity of the dispersion and substrate were printed onto samples of the following substrates: glass fibre filter paper GC-50 (Advanetc); glass microfiber filter GF/B (Whatman); nylon membrane filter 0.2 μm (Phenomenex); filter paper 1 (Whatman); polypropylene filter membrane (Gelman Sciences); METRICEL™ filter membrane GA-3 1.2 μm (Gelman Sciences); TEFLON™ filter membrane TF-200 0.2 μm (Gelman Instrument Company); glass fibre filter A/E (Pall Life Sciences), nylon 66 filter membrane 0.45 μm (Schleicher & Schuell) and silk. The printed samples of substrate were then immersed in a solution of 2% (w/v) bovine serum albumin (BSA) in PBS for 1 hour prior to being rinsed and the surface of the substrate being flooded with a 1 in 5 dilution in BSA of anti-B immunoglobulin (EPICLONE™ monoclonal, CSL Limited) and incubated for 30 minutes. The surfaces of the substrates were then washed 6 times with PBS prior to being flooded with a 1:400 dilution of alkaline phosphatase conjugated sheep anti-mouse immunoglobulin (Chemicon) and incubated for 30 minutes. The surfaces of the substrates were then washed 6 times with PBS followed by a washing of substrate buffer (100 mM Tris, 100 mM NaCl, 50 mM $MgCl_2$, pH 9.5). The substrate buffer washed surfaces of the substrates were then flooded with a 1 in 50 dilution in substrate buffer of the chromogenic substrate (18.75 mg/mL nitro blue tetrazolium chloride and 9.4 mg/mL 5-bromo-4-chloro-3-indolyl phosphate, toluidine salt) (NBTC-BCIP) in 67% DMSO (Roche)) for about 10 minutes. The chromogenic reaction was stopped by rinsing the surface of each substrate with deionised water. The appearance of the surface of each substrate following incubation with the chromogenic substrate is provided in FIG. 5. It will be observed that there was no immunostaining of the surface of the substrate in the region where the monoacyl counterpart (monoacyl-B) of the construct $B_{tri}$-sp-Ad-DOPE (FSL-B) was printed. It is assumed that the monoacyl counterpart was washed away during the immunostaining procedure.

EXAMPLE 3

Dispersions of the constructs FSL-A and FSL-Biotin at a concentration of 0.5 mg/ml (circa 6 mM) in PBS were painted onto glass fibre threads using a brush. The painted thread was allowed to dry between applications of subsequent layers.

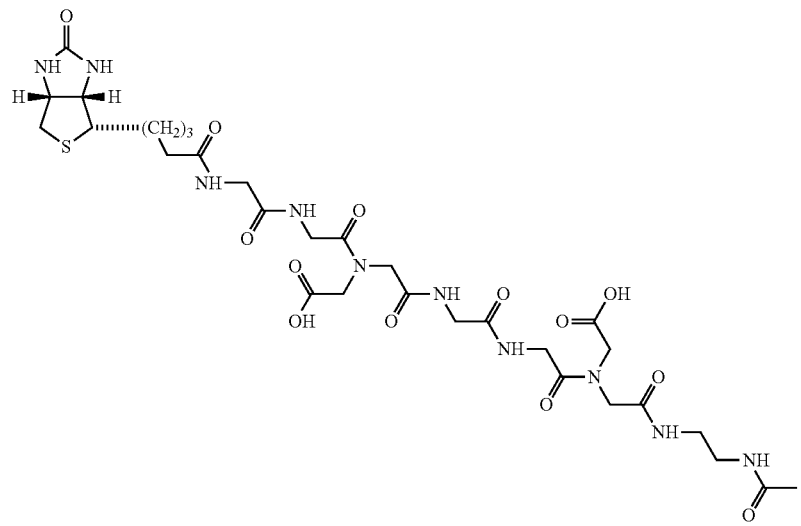

-continued

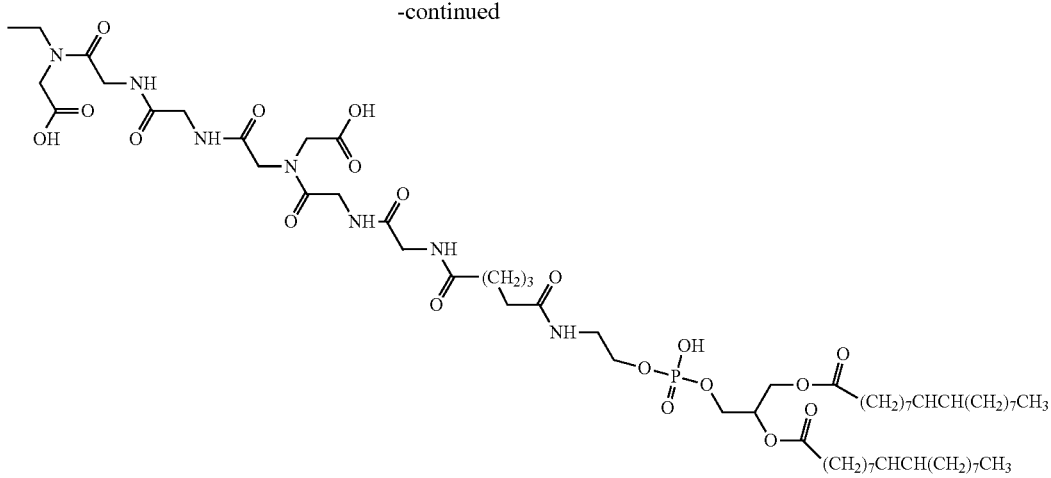

FSL-Biotin (as described in the specification accompanying international application no. PCT/NZ2008/000266 (publ. no. WO 2009/048343))

Figure 6:
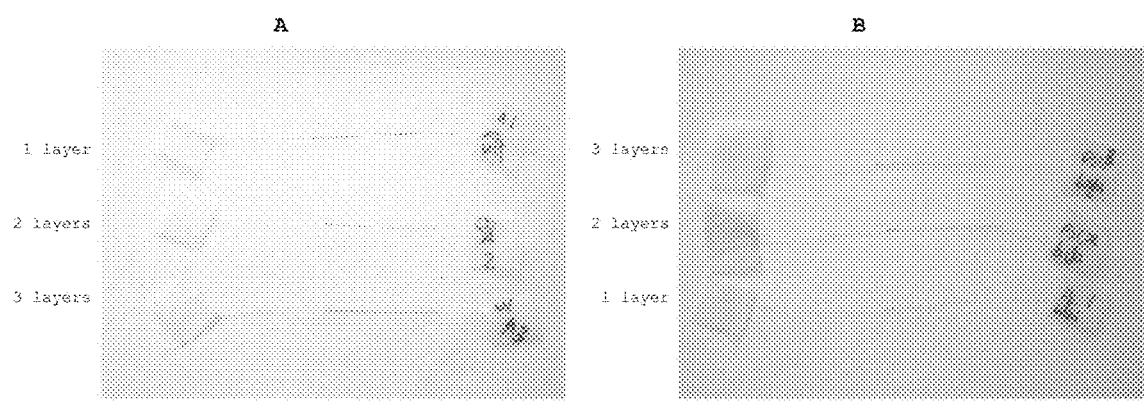
FIG. 6. Appearance of fibre glass threads painted with layers of FSL-A and FSL-Biotin following immunostaining according to the method described in Example 3. The left hand end of the thread has not been painted.

A glass fibre thread painted with 1 to 3 layers of the dispersion of FSL-A was immersed in a solution of 2% (w/v) bovine serum albumin (BSA) in PBS for 1 hour prior to being rinsed and immersed in a 1 in 5 dilution in BSA of anti-B immunoglobulin (EPICLONE™ monoclonal, CSL Limited) for 30 minutes. The painted glass fibre thread was then washed 6 times with PBS prior to being immersed in a 1:400 dilution of alkaline phosphatase conjugated sheep anti-mouse immunoglobulin (Chemicon) for 30 minutes. The thread was then washed 6 times with PBS followed by a washing of substrate buffer (100 mM Tris, 100 mM NaCl, 50 mM $MgCl_2$, pH 9.5). The washed thread was then immersed in a 1 in 50 dilution in substrate buffer of the chromogenic substrate (18.75 mg/mL nitro blue tetrazolium chloride and 9.4 mg/mL 5-bromo-4-chloro-3-indolyl phosphate, toluidine salt) (NBTC-BCIP) in 67% DMSO (Roche)) for about 10 minutes. The chromogenic reaction was stopped by immersing the thread in deionised water. The appearance of threads coated with 1, 2 or 3 layers of FSL-A following incubation with the chromogenic substrate is provided in FIG. 6A.

A glass fibre thread painted with 1 to 3 layers of the dispersion of FSL-Biotin was immersed in a solution of 2 μg/mL streptavidin-alkaline phosphatase conjugate in bovine serum albumin (BSA) in PBS for 1 hour prior to being washed 6 times with PBS followed by a washing of substrate buffer (100 mM Tris, 100 mM NaCl, 50 mM $MgCl_2$, pH 9.5). The washed thread was then immersed in a 1 in 50 dilution in substrate buffer of the chromogenic substrate (18.75 mg/mL nitro blue tetrazolium chloride and 9.4 mg/mL 5-bromo-4-chloro-3-indolyl phosphate, toluidine salt) (NBTC-BCIP) in 67% DMSO (Roche)) for about 15 minutes. The chromogenic reaction was stopped by immersing the thread in deionised water. The appearance of threads coated with 1, 2 or 3 layers of FSL-Biotin following incubation with the chromogenic substrate is provided in FIG. 6B.

Figure 7:
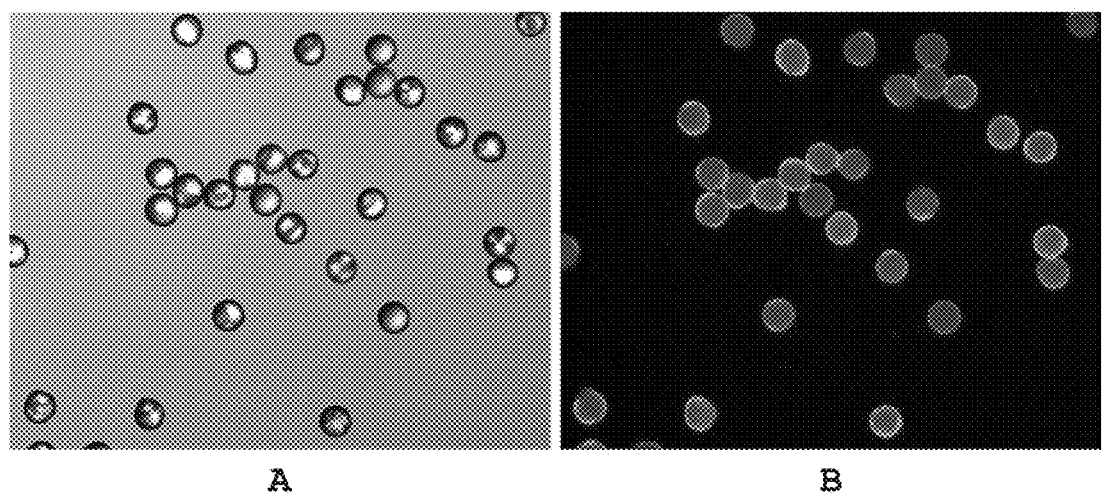
FIG. 7. Photomicrographs of functionalised polycarbonate microspheres (the surface of which has been functionalised using the construct designated FSL-Biotin) following mixing with a solution of avidin conjugated AlexaFlour™ 488 and examined by light (A) and fluorescent (B) microscopy.
Figure 8:
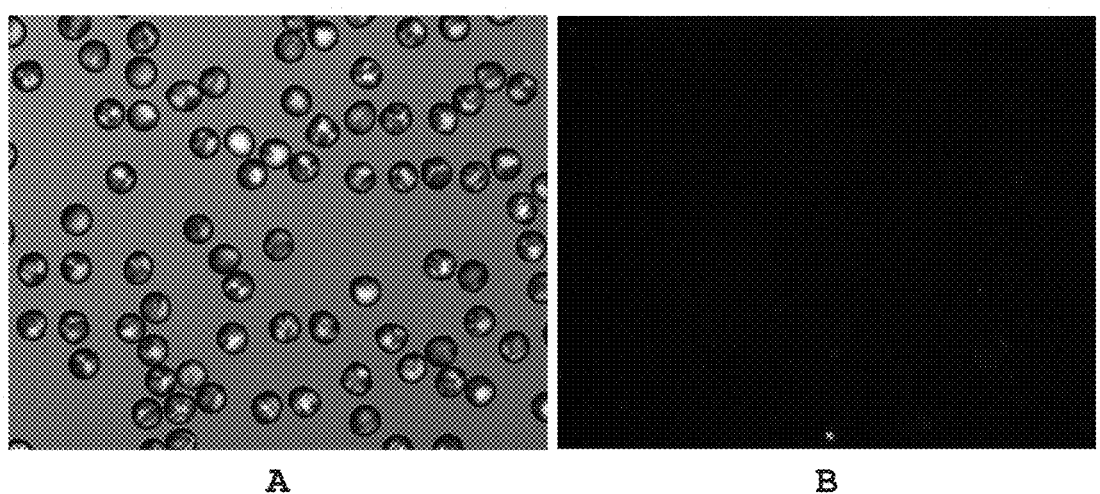
FIG. 8. Photomicrographs of untreated (control) polycarbonate microspheres (cf.
Figure 9:
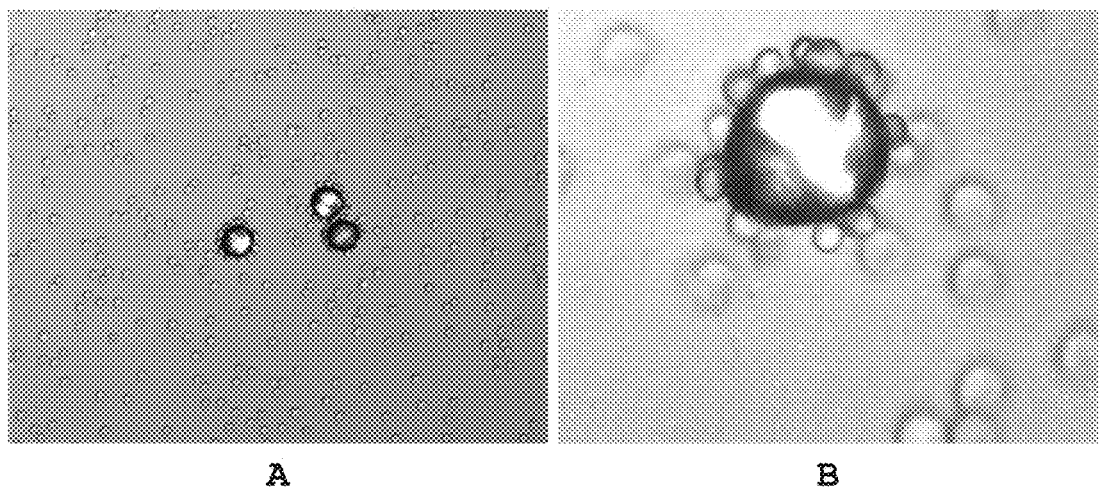
FIG. 9. Photomicrographs of functionalised polycarbonate microspheres (the surface of which has been functionalised using the construct designated FSL-Biotin) following mixing with a solution of streptavidin then FSL-Biotin kodecytes (RBCS) [20× magnification (A), 100× magnification (B)].

The ability to functionalise the otherwise inert surface of a substrate allows a number of novel applications to be developed. For example, immunosorbent assays may be performed with greater facility using laboratory filter assemblies such as those illustrated in cross section in FIG. 7. It will be appreciated by those skilled in the art that the separate steps of an immunosorbent assay as described in Examples 1, 2 and 3 could be readily performed in such a filter assembly using the method of the invention.

EXAMPLE 4

Localising Functional Moieties to the Surface of Monodisperse Polycarbonate Microspheres An aliquot (2 to 3 μL) of polycarbonate microspheres (MAKROLON™ 2808, Nanomi B.V.) of uniform diameter (20 μM±3%) (monodisperse) was mixed with a 30 μL volume of a 500 μg/mL dispersion in PBS of the construct designated FSL-Biotin. The mixture was incubated at room temperature (circa 22° C.) for 30 minutes prior to washing of the microspheres by repeated (three times) centrifugation and resuspension in PBS. The functionalised and washed microspheres were finally resuspended in a volume of 200 μL of PBS. An aliquot (2 to 3 μL) of the same polycarbonate microspheres were also suspended in a volume of 200 μL of PBS without prior mixing with a dispersion of construct and used as a control.

A 50 μL volume of the suspension of functionalised and washed microspheres was mixed with a 50 μL volume of a 100 μg/mL solution in PBS of avidin conjugated AlexaFlour™ 488 (Life Technologies). Similarly, a 50 μL volume of the suspension of untreated (control) polycarbonate microspheres was mixed with a 50 μL volume of a 100 μL/mL solution in PBS of avidin conjugated AlexaFlour™ 488 (Life Technologies). Both mixtures were incubated at 37° C. for 30 minutes prior to washing of the microspheres by repeated (three times) centrifugation and resuspension in PBS as before. The washed microspheres were resuspended in a volume of PBS sufficient to permit examination by light and fluorescence microscopy. Only the functionalised microspheres were observed to fluoresce (see FIG. 7 and FIG. 7).

EXAMPLE 5

Localising RBCs to the Surface of Monodisperse Polycarbonate Microspheres via Avidin-Biotin Conjugation Biotin was localised to the surface of O-group RBCs using the construct designated FSL-Biotin. A 50 μL volume of packed RBCs was mixed with a 50 μL volume of a 200 μg/mL dispersion of PBS of the construct. The mixture was incubated at 37° C. for 2 hours prior to washing of the cells by repeated (three times) centrifugation and resuspension in PBS. The washed and modified RBCs (kodecytes) were finally resuspended in a volume of PBS at a density of 20% of the PCV.

An aliquot (2 to 3 μL) of polycarbonate microspheres (MAKROLON™ 2808, Nanomi B.V.) of uniform diameter (20 μM±3%) (monodisperse) was mixed with a 30 μL volume of a 200 μg/mL dispersion in PBS of the construct designated FSL-Biotin. The mixture was incubated at room temperature (circa 22° C.) for 30 minutes prior to washing of the functionalised microspheres by repeated (three times) centrifugation and resuspension in PBS. The functionalised and washed microspheres were finally resuspended in a volume of 200 μL of PBS.

A 50 μL volume of the suspension of the functionalised and washed microspheres was mixed with a 50 μL volume of a 200 μg/mL solution in PBS of streptavidin and the mixture incubated at room temperature (circa 22° C.) for 30 minutes. Following incubation the avidinylated functionalised microspheres were washed by repeated (three times) centrifugation and resuspended in PBS.

Figure 10:
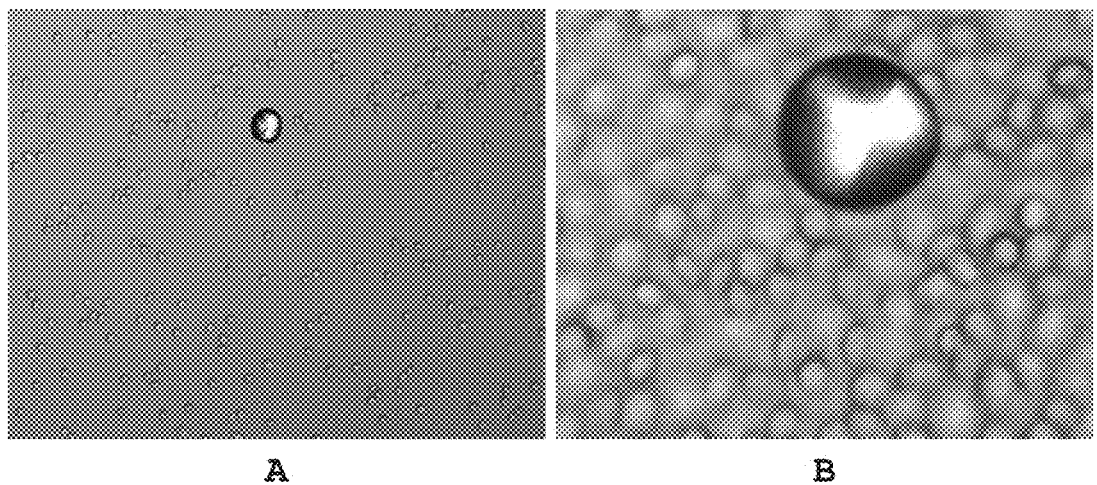
FIG. 10. Photomicrographs of untreated (control) polycarbonate microspheres (cf.
Figure 11:
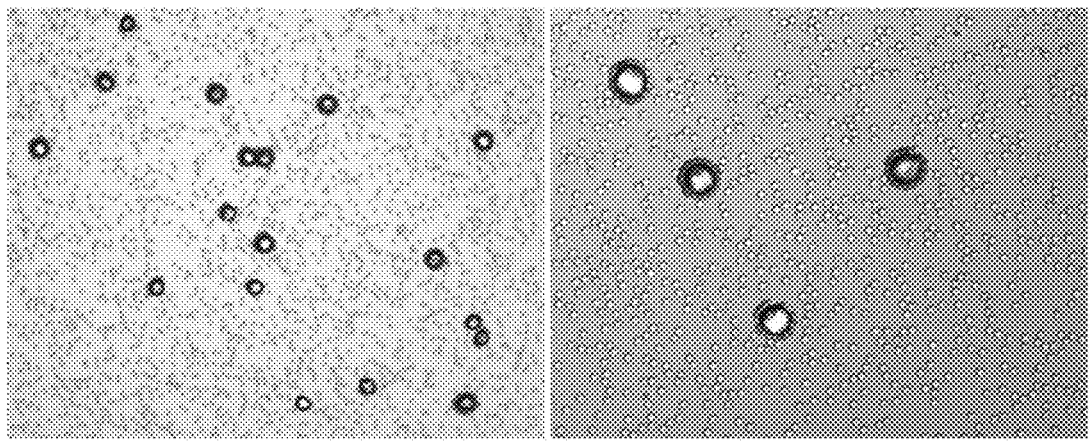
FIG. 11. Photomicrographs of functionalised polycarbonate microspheres (the surface of which has been functionalised using the construct designated FSL-$A_{tri}$) following mixing with a solution of monoclonal anti-A (Epiclone, CSL Limited) then FSL-$A_{tri}$ kodecytes (RBCs) [10× magnification (A), 20× magnification (B), 100× magnification, first focal plane (C), 100× magnification, second focal plane (D)].
Figure 11:
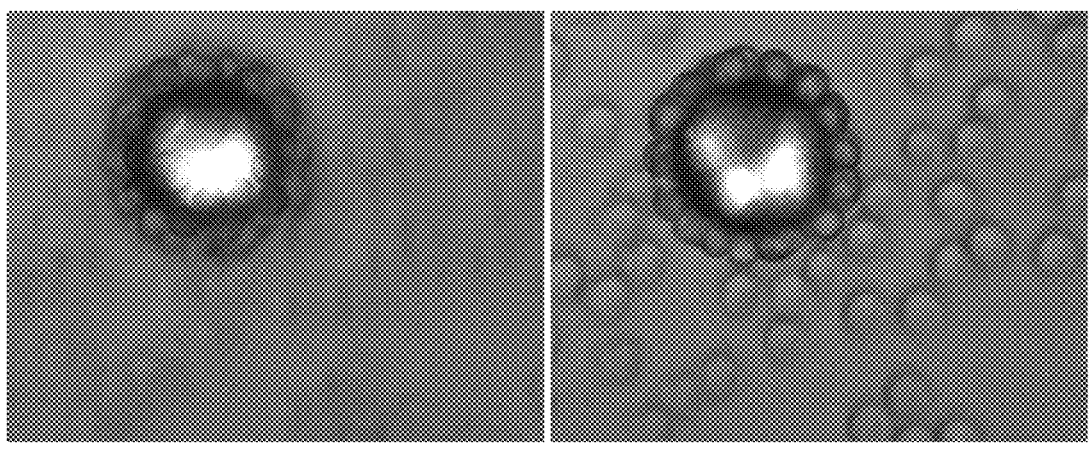

A 50 μL volume of the FSL-Biotin kodecytes suspended in PBS at a density of 20% PCV was mixed with a 20 μL volume of the suspension of avidinylated functionalised microspheres. A 20 μL volume of O-group RBCs resuspended in PBS at a density of 20% PCV was mixed with a 20 μL volume of the avidinylated functionalised microspheres as a control. Both mixtures were incubated at 37° C. for 1½ hours before dilution with 100 μL PBS to permit viewing by light microscopy. FSL-Biotin kodecytes were observed to be localised to the surface of the avidinylated functionalised microspheres only (see FIG. 10 and FIG. 11).

EXAMPLE 6

Localising RBCs to the Surface of Monodisperse Polycarbonate Microspheres via Antibody-Antigen Cross-Reactivity Blood group A-antigen ($A_{tri}$) was localised to the surface of O-group RBCs using the construct designated FSL-$A_{tri}$. A 50 μL volume of the packed RBCs was mixed with a 50 μL volume of a 200 μg/mL dispersion in PBS of the construct. The mixture was incubated at 37° C. for 2 hours prior to washing of the cells by repeated (three times) centrifugation and resuspension in PBS. The washed and modified RBCs (kodecytes) were finally resuspended in a volume of PBS at a density of 20% of the PCV.

An aliquot (2 to 3 μL) of polycarbonate microspheres (MAKROLON™ 2808, Nanomi B.V.) of uniform diameter (20 μM±3%) (monodisperse) was mixed with a 30 μL volume of a 200 μg/mL dispersion in PBS of the construct designated FSL-$A_{tri}$. The mixture was incubated at room temperature (circa 22° C.) for 30 minutes prior to washing of the functionalised microspheres by repeated (three times) centrifugation and resuspension in PBS. The functionalised and washed microspheres were finally resuspended in a volume of 200 μL of PBS.

A 50 μL volume of the suspension of the functionalised and washed microspheres was mixed with a 50 μL volume of undiluted monoclonal anti-A (Epiclone, CSL Limited) and the mixture incubated at room temperature (circa 22° C.) for 60 minutes. Following incubation the antibody bound functionalised microspheres were washed by repeated (three times) centrifugation and resuspended in PBS.

A 20 μL volume of the suspension of FSL-$A_{tri}$ kodecytes resuspended in PBS at a density of 20% PCV was mixed with a 20 μL volume of the antibody bound functionalised microspheres. A 20 μL volume of O-group RBCs resuspended in PBS at a density of 20% PCV was mixed with a 20 μL volume of the suspension of the antibody bound functionalised microspheres as a first control. A 20 μL volume of the suspension of FSL-$A_{tri}$ kodecytes resuspended in PBS at a density of 20% PCV was mixed with a 20 μL volume of the functionalised microspheres obtained prior to mixing and incubation with the undiluted monoclonal anti-A (Epiclone, CSL Limited) as a second control. All mixtures were incubated at room temperature (circa 22° C.) for 1½ hours before dilution by the addition of a 200 μL volume of PBS to permit viewing by light microscopy.

Figure 12:
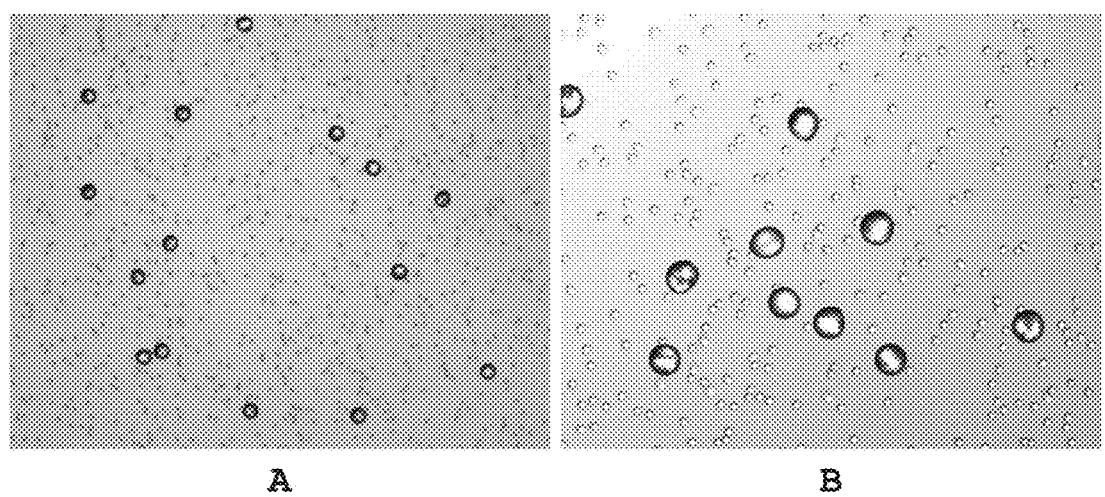
FIG. 12. Photomicrographs of functionalised polycarbonate microspheres (the surface of which has been functionalised using the construct designated FSL-A$_{tri}$) following mixing with a solution of monoclonal anti-A (Epiclone, CSL Limited) then O-group RBCs [10× magnification (A), 20× magnification (B)].
Figure 13:
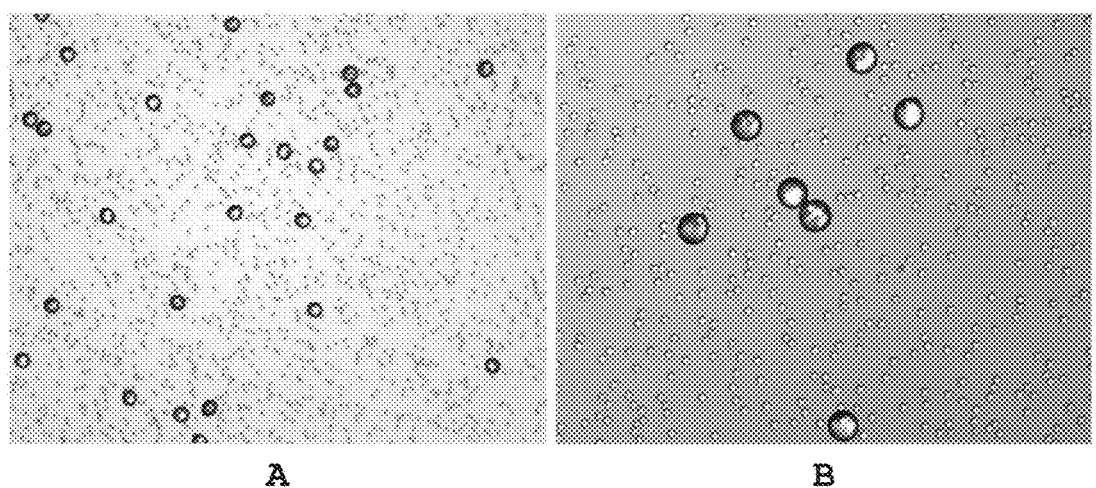
FIG. 13. Photomicrographs of functionalised polycarbonate microspheres (the surface of which has been functionalised using the construct designated FSL-A$_{tri}$) following mixing with FSL-A$_{tri}$ kodecytes (RBCs) in the absence of monoclonal anti-A (Epiclone, CSL Limited) [10× magnification (A), 20× magnification (B)].
Figure 14:
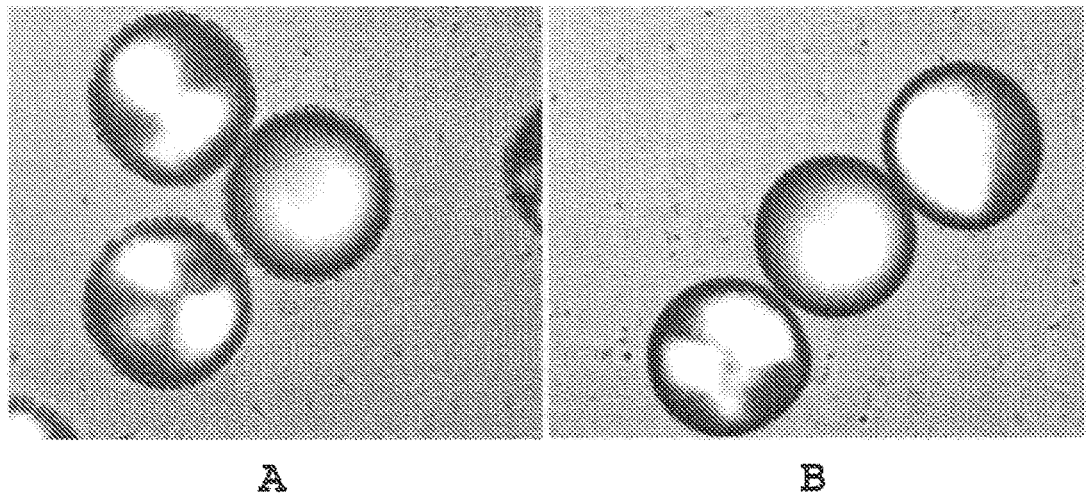
FIG. 14. Photomicrographs of functionalised polycarbonate microspheres (the surface of which has been functionalised using the construct designated FSL-Biotin) (A) and untreated (control) polycarbonate microspheres (B) following mixing with FSL-A$_{tri}$ bacteria (*Staphylococcus sarophyticus*).

RBCs were observed to be localised to the surface of the treated and washed polycarbonate microspheres only where antibody was present (see FIG. 12, FIG. 13 and FIG. 14).

EXAMPLE 7

Localising Bacteria to the Surface of Monodisperse Polycarbonate Microspheres via Avidin-Biotin Conjugation Biotin was localised to the surface of two species of bacterium (*Staphylococcus sarophyticus* and *Micrococcus luteus*) using the construct designated FSL-Biotin. A 50 μL volume of a 200 μg/mL dispersion in PBS of the construct was mixed with a colony of each bacterium. Each mixture was incubated at 37° C. for 2 hours prior to washing of the bacterial cells by repeated (three times) centrifugation and resuspension in PBS. The washed and treated bacterial cells were finally resuspended in a 300 μL volume of PBS.

An aliquot (2 to 3 μL) of polycarbonate microspheres (MAKROLON™ 2808, Nanomi B.V.) of uniform diameter (20 μM±3%) (monodisperse) was mixed with a 30 μL volume of a 200 μg/mL dispersion in PBS of the construct designated FSL-Biotin. The mixture was incubated at room temperature (circa 22° C.) for 30 minutes prior to washing of the functionalised microspheres by repeated (three times) centrifugation and resuspension in PBS. The functionalised microspheres were finally resuspended in a volume of 200 μL of PBS. A 50 μL volume of the functionalised microspheres was mixed with a 50 μL volume of a 2 mg/mL solution in PBS of avidin and the mixture incubated at room temperature (circa 22° C.) for 30 minutes. Following incubation the avidinylated functionalised microspheres were washed by repeated (three times) centrifugation and resuspension in PBS.

Figure 15:
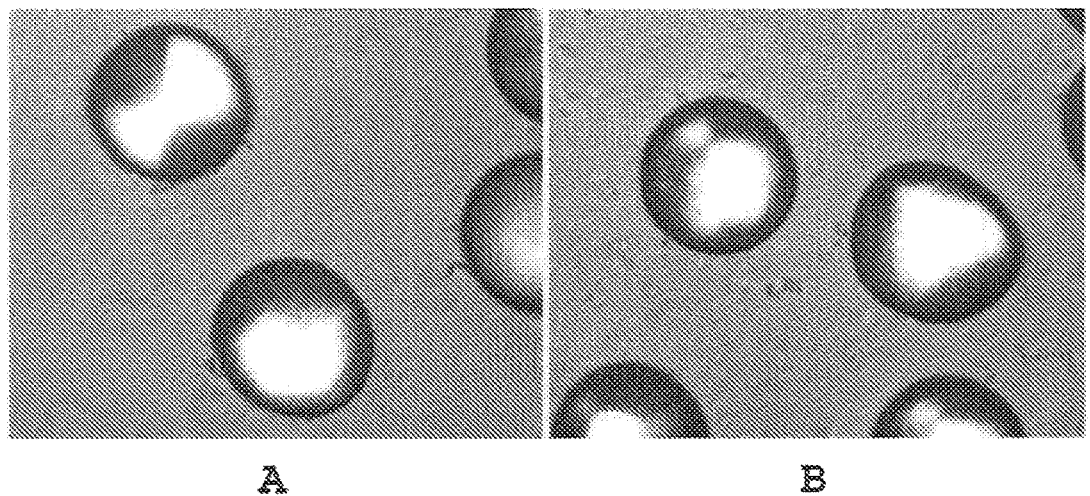
FIG. 15. Photomicrographs of functionalised polycarbonate microspheres (the surface of which has been functionalised using the construct designated FSL-Biotin) (A) and untreated (control) polycarbonate microspheres (B) following mixing with FSL-A$_{tri}$ bacteria (*Micrococcus luteus*).
Figure 16:
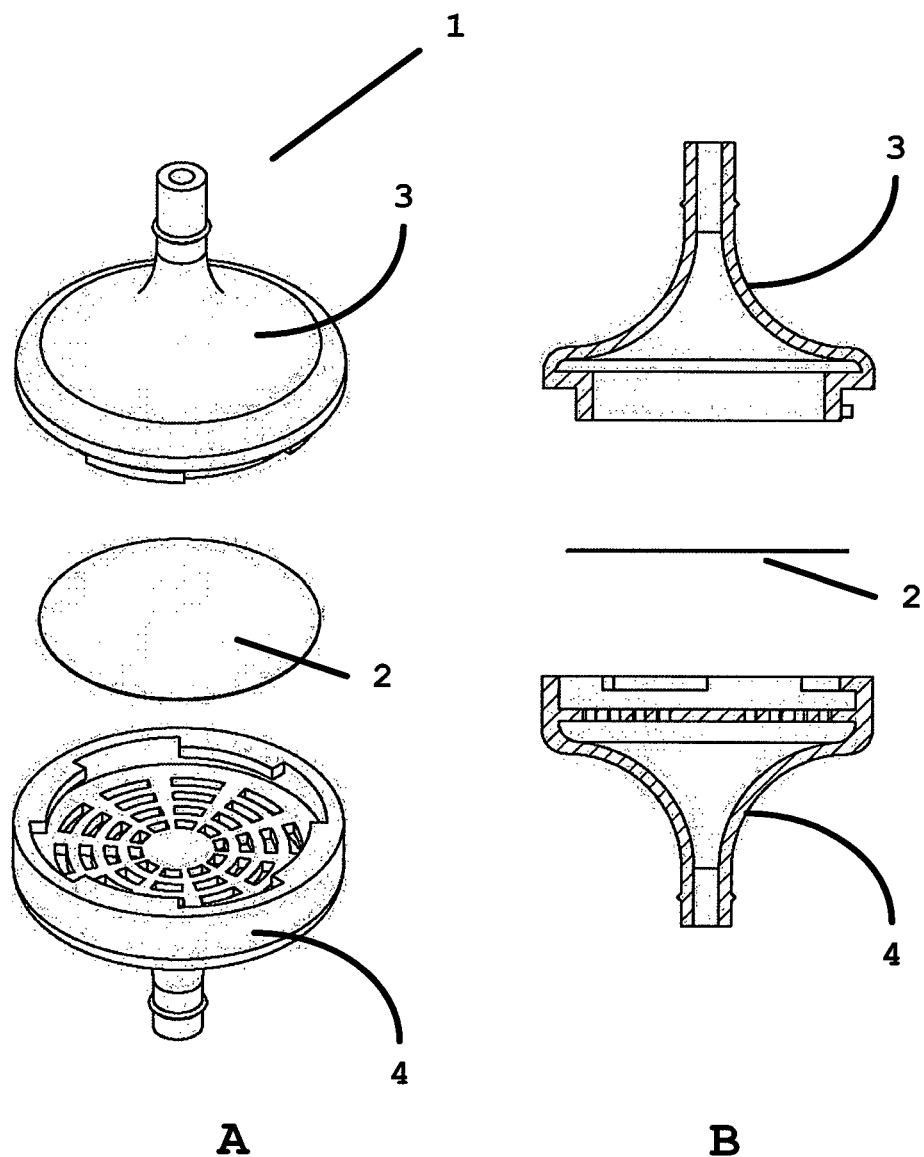
FIG. 16. Perspective (A) and side (B) views of a disassembled filter assembly (1) comprising a functionalised porous membrane (2) prepared according to the method of the first aspect of the invention and sealed between an inlet housing (3) and an outlet housing (4).
Figure 17:
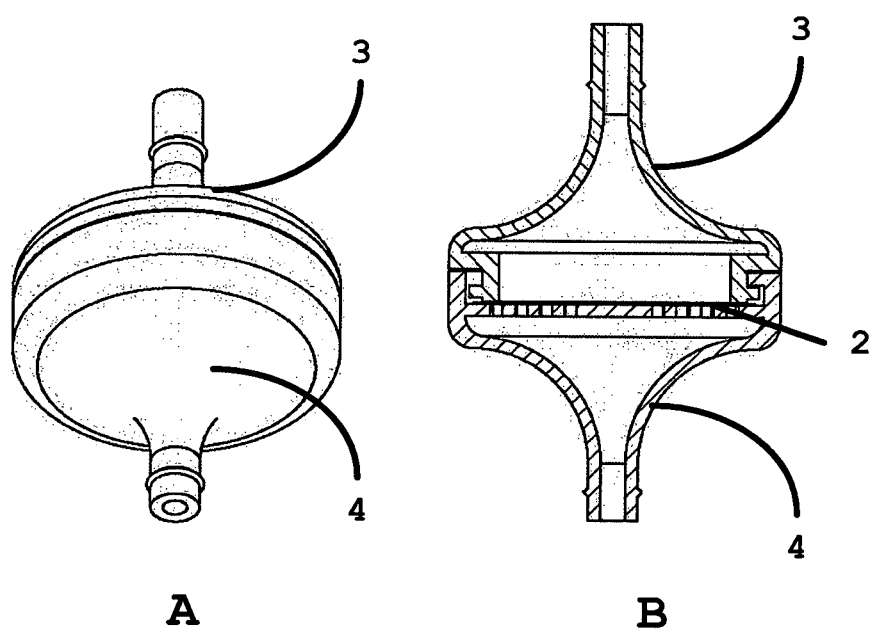
FIG. 17. Perspective (A) and side (B) views of the assembled filter assembly comprising a functionalised porous membrane (2) prepared according to the method of the first aspect of the invention and sealed between an inlet housing (3) and an outlet housing (4).

A 50 μL volume of the suspension of FSL-Biotin modified bacterial cells was mixed with a 50 μL volume of the avidinylated functionalised microspheres. The mixture was incubated at room temperature (circa 22° C.) for 30 minutes before examination by light microscopy. Bacterial cells were observed to be localised to the surface of the avidinylated functionalised microspheres (see FIG. 15 and FIG. 16).

Although the invention has been described with reference to embodiments or examples it should be appreciated that variations and modifications may be made to these embodiments or examples without departing from the scope of the invention. Where known equivalents exist to specific elements, features or integers, such equivalents are incorporated as if specifically referred to in this specification. In particular, variations and modifications to the embodiments or examples that include elements, features or integers disclosed in and selected from the referenced publications are within the scope of the invention unless specifically disclaimed. The advantages provided by the invention and discussed in the description may be provided in the alternative or in combination in these different embodiments of the invention. Although the invention has been described with reference to embodiments or examples it should be appreciated that variations and modifications may be made to these embodiments or examples without departing from the scope of the invention. Where known equivalents exist to specific elements, features or integers, such equivalents are incorporated as if specifically referred to in this specification. In particular, variations and modifications to the embodiments or examples that include elements, features or integers disclosed in and selected from the referenced publications are within the scope of the invention unless specifically disclaimed. The advantages provided by the invention and discussed in the description may be provided in the alternative or in combination in these different embodiments of the invention.

The invention claimed is:

1. A method of functionalising microspheres comprising the steps of:
   immersing the microspheres in an aqueous dispersion of a construct of the structure F-S-L; and then
   washing the microspheres with an aqueous vehicle to provide the functionalised microspheres,
   where the construct is a construct of the structure:

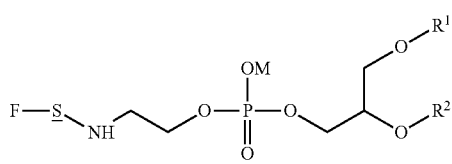

where F is a functional moiety, M is a monovalent cation, $R^1$ and $R^2$ are independently a $C_{14-20}$ acyl, alkyl or alkenyl group, and S is a spacer selected to provide a construct that is dispersible in water; and where the microsphere is a polycarbonate microsphere.

2. The method of claim 1 where the construct is a construct of the structure:

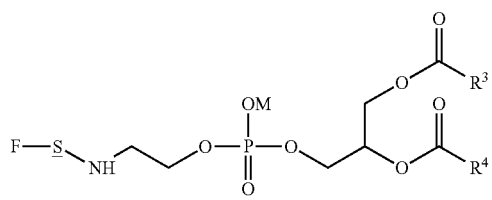

where $R^3$ and $R^4$ are independently a $C_{13-19}$ alkyl or alkenyl group.

3. The method of claim 2 where $R^3$ and $R^4$ are independently a $C_{15-17}$ alkyl or alkenyl group.

4. The method of claim 3 where the construct is a construct of the structure:

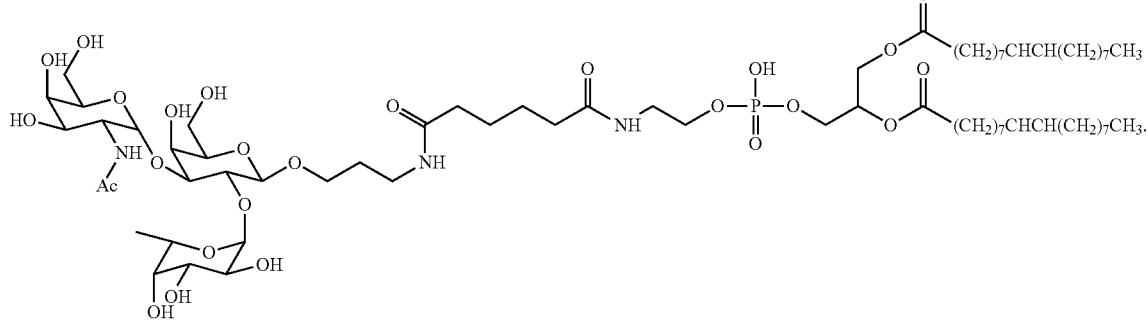

* * * * *